(12) United States Patent
Hackert (10) Patent No.: US 10,806,815 B2
(45) Date of Patent: Oct. 20, 2020

(54) FLOOR PROCESSING DEVICE WITH A MOTOR-DRIVEN FLOOR PROCESSING ELEMENT

(71) Applicant: Vorwerk & Co. Interholding GmbH, Wuppertal (DE)

(72) Inventor: Georg Hackert, Bochum (DE)

(73) Assignee: Vorwerk & Co. Interholding GmbH, Wuppertal (DE)

( * ) Notice: Subject to any disclaimer, the term of this patent is extended or adjusted under 35 U.S.C. 154(b) by 215 days.

(21) Appl. No.: 16/039,706

(22) Filed: Jul. 19, 2018

(65) Prior Publication Data
US 2019/0022269 A1    Jan. 24, 2019

(30) Foreign Application Priority Data
Jul. 20, 2017  (DE) .......................... 10 2017 116 363

(51) Int. Cl.
| | |
|---|---|
| *A61L 9/12* | (2006.01) |
| *A47L 11/24* | (2006.01) |
| *A47L 11/40* | (2006.01) |
| *A47L 7/00* | (2006.01) |
| *A47L 9/04* | (2006.01) |

(52) U.S. Cl.
CPC ............... *A61L 9/12* (2013.01); *A47L 7/009* (2013.01); *A47L 9/0477* (2013.01); *A47L 11/24* (2013.01); *A47L 11/4041* (2013.01); *A47L 2201/00* (2013.01); *A61L 2209/134* (2013.01)

(58) Field of Classification Search
CPC .. A47L 11/24; A47L 11/4041; A47L 2201/00; A47L 7/009; A47L 9/0477; A61L 2209/134; A61L 9/12
See application file for complete search history.

(56) References Cited

U.S. PATENT DOCUMENTS

| | | | |
|---|---|---|---|
| 6,511,548 B1 * | 1/2003 | Oreck ....................... | A47L 7/04 134/21 |
| 2004/0103490 A1 * | 6/2004 | Long ..................... | A47L 11/125 15/22.1 |
| 2005/0224595 A1 * | 10/2005 | Kuiper ..................... | A47L 7/04 239/59 |
| 2005/0229340 A1 * | 10/2005 | Sawalski ................. | A47L 11/24 15/50.3 |
| 2006/0190133 A1 * | 8/2006 | Konandreas ....... | A22C 17/0013 700/245 |
| 2007/0016328 A1 * | 1/2007 | Ziegler ..................... | A47L 5/14 700/245 |

(Continued)

FOREIGN PATENT DOCUMENTS

| | | |
|---|---|---|
| DE | 102 09 298 A1 | 9/2003 |
| DE | 20 2007 017 026 U1 | 4/2009 |

(Continued)

OTHER PUBLICATIONS

KR-20050013867-A—English Machine Translation (Year: 2005).*

*Primary Examiner* — Marc Carlson
(74) *Attorney, Agent, or Firm* — Collard & Roe, P.C.

(57) ABSTRACT

A floor processing device has a motor-driven floor processing element for processing a floor to be processed, wherein the floor processing element has a hollow space with a hollow space opening that joins the hollow space with the ambient air. A fragrance element is arranged in the hollow space.

12 Claims, 5 Drawing Sheets

(56) References Cited

U.S. PATENT DOCUMENTS

| | | | |
|---|---|---|---|
| 2007/0079470 A1* | 4/2007 | Rippl | A47L 11/405 15/320 |
| 2011/0130877 A1* | 6/2011 | Lynch | A47L 7/04 700/258 |
| 2012/0145189 A1* | 6/2012 | Knopow | A47L 13/16 134/6 |
| 2012/0145191 A1* | 6/2012 | Williams | A47L 13/17 134/6 |
| 2014/0331443 A1* | 11/2014 | Houghton | A47L 13/225 15/320 |
| 2017/0231455 A1* | 8/2017 | Krebs | B08B 3/106 15/320 |
| 2018/0168418 A1* | 6/2018 | Pfeiffer | A47L 11/14 |

FOREIGN PATENT DOCUMENTS

| | | | |
|---|---|---|---|
| KR | 20050013867 A | * | 2/2005 |
| KR | 20140111819 A | * | 9/2014 |

* cited by examiner

FLOOR PROCESSING DEVICE WITH A MOTOR-DRIVEN FLOOR PROCESSING ELEMENT

CROSS REFERENCE TO RELATED APPLICATIONS

Applicant claims priority under 35 U.S.C. § 119 of European Application No. 10 2017 116 363.8, filed Jul. 20, 2017, the disclosure of which is incorporated by reference.

BACKGROUND OF THE INVENTION

1. Field of the Invention

The invention relates to a floor processing device with a motor-driven floor processing element for processing a floor to be processed, wherein the floor processing element has a hollow space with a hollow space opening that joins the hollow space with the ambient air.

2. Description of the Related Art

Floor processing devices with motor-driven floor processing elements are sufficiently known in prior art.

For example, floor processing devices of this kind can be vacuuming devices or wet wiping devices, which have a floor processing element that is driven so as to oscillate or rotate. For example, the floor processing element can be a cleaning roller that can rotate around a rotational axis, which is equipped with a cleaning layer or bristle elements. For example, publication DE 20 2007 017 026 U1 shows such a floor processing device.

Also known are floor processing devices that have no cleaning task, but rather perform a polishing task, sanding task or the like, for example. Furthermore, floor processing devices are here also to be understood as devices which can be used to clean surfaces above the floor. The floor processing devices can either be floor processing devices that are manually guided by the user, or floor processing devices that can automatically move within an environment, for example, in particular autonomous robots.

Also known is to equip cleaning devices with fragrance elements, so as to impart a fragrance to the exhaust air emitted by the cleaning device. Known from publication DE 102 09 298 A1, for example, is to equip the exhaust air side of a filter bag for a cleaning device with a fragrance element, which is swept over by exhaust air exiting the filter bag.

The known floor processing devices with fragrance elements are designed in such a way that the fragrance emanating from the fragrance element is conveyed into the environment by an exhaust air generated by a motor-fan unit of the cleaning device.

SUMMARY OF THE INVENTION

Proceeding from the aforementioned prior art, the object of the invention involves a floor processing device with an alternatively arranged fragrance element.

In order to achieve the aforementioned object, the invention proposes a floor processing device with a motor-driven floor processing element for processing a surface to be processed, wherein the floor processing element has a hollow space with a hollow space opening that joins the hollow space with the ambient air, wherein a fragrance element is arranged in the hollow space.

According to the invention, the floor processing device is equipped with a fragrance element, which is displaced while driving the floor processing element, and can emit fragrance molecules through the hollow space opening into the ambient air because of the displacement and air movement associated therewith. In an especially simple embodiment, the fragrance flows out of the hollow space just based on the air flows that are caused by centrifugal forces and sweep by the fragrance element. The fragrance element is preferably detachably arranged in the hollow space, wherein a wall of the hollow space has an opening, for example also a hollow space opening, which at least relative to a dimension is larger than a dimension of the fragrance element, so that the latter can be removed from the hollow space. The fragrance of the fragrance element spreads more intensively through the ambient air in particular when the floor processing element is driven, i.e., driven so as to rotate or oscillate. In particular given an autonomously moving floor processing device, this provides the user of the floor processing device with an indication that the floor processing device has performed a floor processing operation, for example a vacuuming or wiping operation. As a consequence, the fragrance is simultaneously a signal that the floor processing device has performed a floor processing activity. For example, given an error in the motor drive of the floor processing element, the fragrance signal is simultaneously absent, thus alerting the user to a malfunction.

In a preferred embodiment, the floor processing element can be a cleaning roller that can rotate around a rotational axis. For example, the cleaning roller can be a wiping roller covered by a cleaning cloth for performing a wet cleaning activity, or also a cleaning roller outwardly equipped with bristle elements for a dry cleaning activity. In particular, the floor processing element can be designed as a kind of hollow cylinder, wherein the fragrance element is arranged inside of the cylinder.

In another embodiment, the floor processing element is be designed like a kind of plate with an interior hollow space, wherein the plate is driven so as to oscillate parallel to the surface to be processed, in particular guided in an eccentric circular movement over the surface to be processed.

It is proposed that a service life of the fragrance element essentially correspond to a service life of a wear part of the floor processing device. In particular, the service life of the fragrance element can essentially correspond to a service life of bristle elements arranged on the floor processing element. As a result of this configuration, a usage time for the fragrance element is coupled to the wear of a wear part of the floor processing device. The wear part can be the floor processing element itself, in particular bristle elements arranged thereon or a cleaning cloth arranged thereon. As a consequence, the user of the floor processing device is notified when the wear part must be replaced. In the event that the wear part is the floor processing element, the fragrance element arranged therein is preferably also replaced at the same time as the floor processing element, so that a floor processing element newly arranged on the floor processing device simultaneously emits a fragrance again. The usage of both the floor processing element and fragrance element depends primarily on the operating time of the floor processing element or fragrance element, so that these timespans can advantageously be synchronized.

It is further proposed that the material of the fragrance element have a lower hardness than the material of a wall bordering the hollow space. In particular, the fragrance element can be made out of a soft elastic material, especially preferably out of a foam. This configuration prevents the fragrance element and wall of the hollow space from audibly colliding with each other while the floor processing element is being driven, and thus moved. As a consequence, a disruptive rattling or rolling noise of the fragrance element inside of the hollow space can be avoided. The soft elastic material can be an open-pored material, in particular a foam, which has pores for absorbing fragrance particles and/or fragrant liquids. In particular, the fragrance element can also be a sponge soaked with a fragrant oil or the like.

In one embodiment, the fragrance element can move freely inside of the hollow space, wherein the hollow space in particular has a volume corresponding to a multiple of the volume of the fragrance element. In this configuration, the fragrance element moves relative to the wall while driving the floor processing element, thus producing additional air turbulences inside of the hollow space. The fragrance of the fragrance element is here distributed, wherein the arising air flow entrains the fragrance molecules, and releases them into the ambient air while exiting through the hollow space opening.

In particular, the hollow space can have a volume corresponding to a multiple of the fragrance element volume. For example, the volume of the hollow space can be 5 times, 10 times, 20 times, 30 times, 40 times up to 100 times or more greater than the volume of the fragrance element, wherein the fragrance element can move freely within the hollow space. It especially makes sense that the geometry of the fragrance element be adjusted to the geometry of the hollow space, for example that a spherical fragrance element can be displaced within a cylindrical hollow space. However, other geometries for the fragrance element are of course also conceivable, for example square, rectangular and/or polygonal geometries. The fragrance element can be held within the hollow space so that it can rotate around a rotational axis, wherein the fragrance element remains rotationally fixed relative to the environment as the floor processing element rotates, while the hollow space rotates around the fragrance element. In addition, the fragrance element can in particular also be designed like a kind of spoked wheel, fan or the like, in the circumferential direction or axial direction of the floor processing element, wherein air turbulence is preferably induced within the hollow space at the same time.

Alternatively, the fragrance element can be non-rotatably arranged on a wall bordering the hollow space. In this configuration, the fragrance element does not move relative to the wall while driving the floor processing element. With no further measures being required, this prevents the fragrance element from hitting a wall of the hollow space, rolling on the wall or otherwise undesirably coming into contact with the wall. As a consequence, disruptive noises are prevented during operation of the floor processing device. In particular, it can be provided that the fragrance element be fixed in a bracket arranged in the hollow space.

In another embodiment, the hollow space can be bordered by two walls that lie one inside the other and can be displaced relative to each other, wherein a first wall has a first hollow space opening, and a second wall has a second hollow space opening, wherein a displacement of the walls relative to each other makes it possible for the first hollow space opening to be closed or opened by the second wall and the second hollow space opening by the first wall. In this configuration, the floor processing element has two walls that run one into the other, which each have at least one hollow space opening. The walls especially preferably each have several hollow space openings, which form a regular or irregular hole pattern within the walls. If the floor processing element is cylindrical in design, the walls can be coaxial hollow cylinders, for example, which rotate relative to each other in the circumferential direction. While operating the floor processing device, i.e., while driving the floor processing element, one of the walls rotates around the other, wherein the hollow space openings regularly or irregularly overlap, and in the process allow or do not allow air enriched with fragrance molecules to exit the hollow space. When the floor processing element is idle, the probability that the hollow space openings of the two walls will overlap must be kept low, so that air charged with fragrance can only exit while the floor processing element is moving. The perceivable fragrance allows the user of the floor processing device to recognize if cleaning has been successfully completed. If the floor processing device is not being used, i.e., the floor processing element is standing idle, the hollow space openings are closed, so that the fragrance of the fragrance element in the ambient air is not discernible.

In an alternative embodiment, the hollow space opening has allocated to it a mechanically activatable valve element, which depending on the level of centrifugal force acting on the valve element due to a rotation of the floor processing element, can be displaced into a closing position that closes the hollow space opening and/or into an opening position that releases the hollow space opening. It here depends on the centrifugal force acting on the valve element whether the hollow space opening is open or not. The term mechanically activatable valve element denotes a valve that operates automatically depending on force, and not a valve to be activated by a user. The underlying knowledge is that a speed-dependent centrifugal force acts on the valve element while the floor processing element rotates. As soon as the centrifugal force outweighs the closing force of the valve element, the valve element opens to let air exit the hollow space. The centrifugal force acting on the valve element here depends primarily on the mass of the valve element and speed of the floor processing element. The hollow space opening is released by the valve element when a defined minimum centrifugal force is exceeded. The valve element is here displaced from the closed position into the open position. In particular, this embodiment is also suitable for floor processing elements whose hollow space stores a liquid, which is intended to escape to the outside through the hollow space opening, for example onto the surface of the floor processing element. In this case, for example, the floor processing element is a cleaning roller moistened from inside, which performs a wet cleaning of the surface to be processed. The fragrance element also located in the hollow space can be used to impart fragrance molecules to the liquid. The user can tell that wet cleaning has occurred based on the fragrant liquid or fragrance molecules left behind on the surface to be cleaned. In the case of a cleaning roller moistened from inside, the exit of liquid from the hollow space depends among other things on the mass of the liquid, the mass of the valve element, the distance of the liquid or valve element from the rotational axis, and the speed of the cleaning roller.

In particular, the valve element can be designed to release the hollow space opening once a minimum speed of the floor processing element has been reached. With respect to otherwise constant parameters, the displacement of the valve element from the closed position into the open position and vice versa depends exclusively on the speed of the cleaning roller around the rotational axis. A minimum speed is here defined, which when exceeded causes the valve element to be displaced into the open position, and thus allows liquid to exit the hollow space. As a consequence, the time at which the hollow space openings are released, and hence the fragrance molecules are able to exit the hollow space, can be specifically controlled by setting the speed of the floor processing element. In this way, fragrance molecules can be effectively prevented from exiting during the mere transport of the floor processing device, during which the floor processing element as a rule does not move.

The valve element can have a restoring element, in particular a spring element, allocated to it, and/or the valve element can be designed as a restoring element, wherein the restoring force of the restoring element acts opposite the centrifugal force in the direction of the closed position. The restoring force of the restoring element acts against the centrifugal force acting on the valve element. The restoring element can be designed separately from the valve element, for example, in the form of a separate pressure spring, tension spring, torsion spring or the like. Alternatively, the valve element itself can be designed as a restoring element, or have the restoring element as an integral component. For example, the valve element can consist of an elastic material, which can be at least partially displaced by the centrifugal force. For example, the valve element can have a film hinge, or have an elastic design in the edge area of the hollow space opening, thereby enabling a displacement based on the acting centrifugal force. The respective restoring element must here be configured in such a way that the restoring force is less than the acting centrifugal force at a defined speed of the floor processing element, so that the valve element opens when the minimum speed is exceeded.

The valve element can have at least one closing element arranged so that it can pivot on a wall of the hollow space. For example, this closing element can be a pivotable valve flap, which is arranged on the edge area of the wall that borders the hollow space opening. The pivotable closing element can either be a separate closing element fastened to the hollow body, or be integrally designed with the hollow body, for example as a film hinge, elastic edge area, or the like.

The valve element can further be a movable, in particular displaceable, closing element arranged on the floor processing element. In addition, the valve element can be an elastically designed edge area of the wall of the hollow space that borders the hollow space opening. In this configuration, the wall has an elastic material at least in the edge area of the hollow space opening, so that the edge area is displaced radially outward by the acting centrifugal force, and the hollow space opening is enlarged. The elastic edge area is advantageously designed in such a way relative to the closed position that overlapping partial areas of the wall are provided in the closed position. In the open position, the partial areas of the wall are spaced apart, thereby releasing the hollow space opening.

All or at least part of the hollow space can have an elastic membrane, wherein at least one hollow space opening is contracted in the closed position and pressed apart in the open position. The hollow space can thus consist of a membrane, for example one having pinprick-like hollow space openings, which open to more or less of an extent depending on the level of acting centrifugal force, and thereby release a flow path for the air and fragrance molecules flowing out of the hollow space. The hollow space openings are thus contracted in points in the closed position, and pressed apart in the open position. It is here recommended that the material selected for the membrane have a modulus of elasticity that permits a rapid opening and closing of the hollow space opening as a function of a change in the level of centrifugal force. In particular, rubbery materials are suitable.

The floor processing device according to the invention can be a wet cleaning device, a dry cleaning device or some other floor processing device, for example a polishing and/or sanding device. It is proposed that the defined minimum speed for the floor processing element measure at least 150 revolutions per minute up to 3,000 revolutions per minute. The indicated minimum speed of 150 revolutions per minute is clearly distinguished from an only random rotation of the floor processing element while transporting the floor transporting device. In like manner, this minimum speed also exceeds the speed of the floor processing element while merely displacing the floor processing device over the surface to be processed. In particular, the indicated speed range corresponds to conventional rotational speeds for the floor processing element during a processing operation for cleaning a surface.

Finally, the floor processing element can have bristle elements pointing radially outward, or be jacketed with a sponge body. It can additionally or alternative be provided that the floor processing element and/or the sponge body be jacketed with a cleaning cloth, in particular a microfiber cloth. For example, this can be a textile cleaning cloth which binds the dirt dissolved from the surface to be processed. Designing the cleaning cloth as a microfiber cloth proves especially advantageous.

BRIEF DESCRIPTION OF THE DRAWINGS

The invention will be described in more detail below based on exemplary embodiments. As shown in the drawings.

DETAILED DESCRIPTION OF THE PREFERRED EMBODIMENTS

Figure 1:
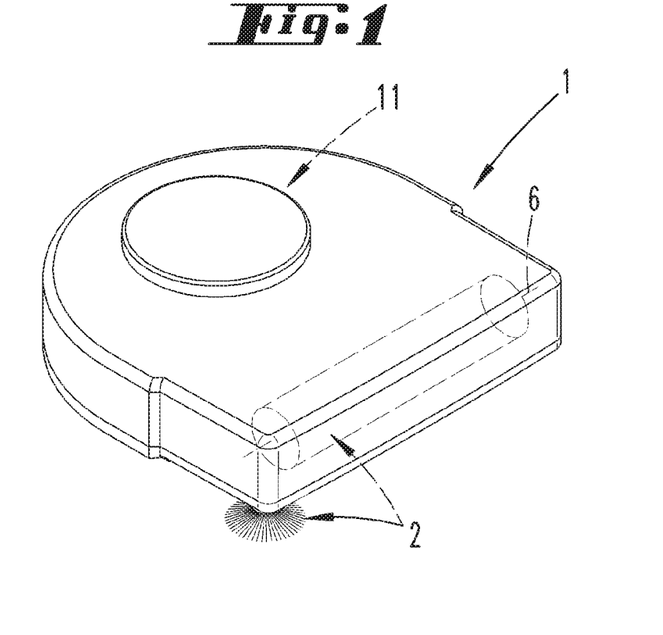
FIG. 1 is a perspective view of a floor processing device.

FIG. 1 shows a floor processing element 1, which is here designed as an automatically moving vacuuming robot. In the usual manner, the floor processing device 1 has a motor-fan unit (not depicted here in more detail) as well as a suction material chamber for receiving dust and dirt. In addition, the floor processing device 1 has a distance measuring device 11, which can be used to measure distances to obstacles within the environment of the floor processing device 1. The distance measuring device 11 here lies within the housing of the floor processing device 1, and is designed as a kind of triangulation measuring device. This triangulation measuring device has a laser diode and a corresponding lens system, so as to guide the light beam emitted by the laser diode out of the floor processing device 1. This light beam then hits obstacles within the environment of the floor processing device 1, and is there reflected and/or scattered. The reflected or scattered light hits a sensor of the distance measuring device 11, and can there be evaluated in reference to a distance of the reflecting or scattering obstacles.

The floor processing device 1 further has several floor processing elements 2, which here include a side brush that protrudes laterally next to the housing of the floor processing device 1, along with a cleaning roller arranged under the floor processing device 1. The floor processing element 2 designed as a cleaning roller is here a cylindrical body having a cylindrical hollow space 3. During the cleaning operation of the floor processing device 1, the floor processing element 2 rotates around a rotational axis 6, which during a conventional cleaning operation of the floor processing device 1 is essentially oriented parallel to a surface to be cleaned.

Figure 2:
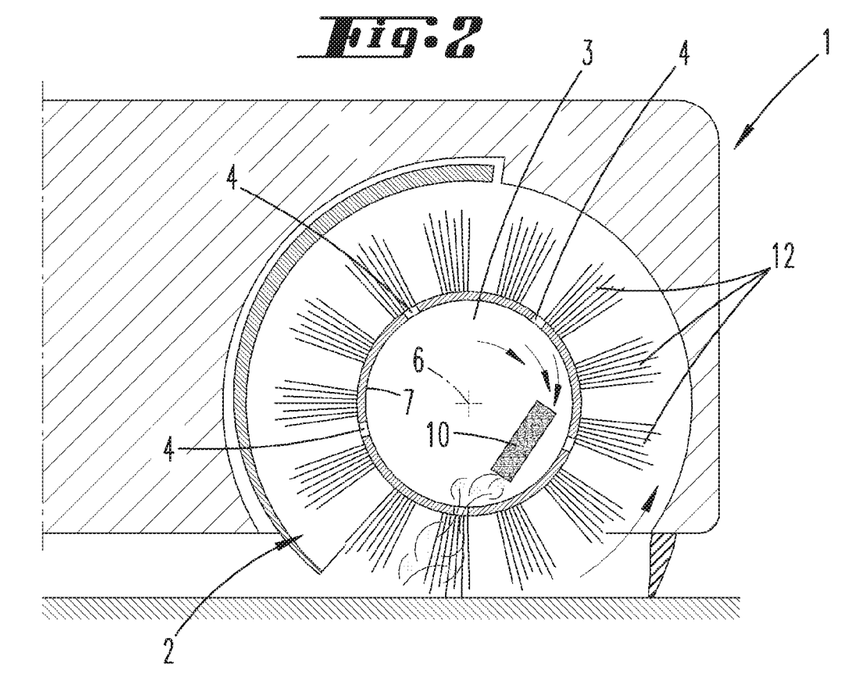
FIG. 2 is a cross section through a floor processing element of the floor processing device according to a first embodiment.

FIG. 2 shows a cross section of the floor processing element 2 transverse to the longitudinal extension of the rotational axis 6. The hollow space 3 is bordered by a wall 7, which has several hollow space openings that join the hollow space 3 of the floor processing element 2 with the ambient air. A fragrance element 10 is arranged within the hollow space 3, and can be freely displaced within the hollow space 3. For example, the fragrance element 10 is here a foam body, the pores of which accommodate an oil that has fragrance molecules. For example, the fragrance element 10 here has an angular cross sectional shape. The hardness of the fragrance element 10 is lower than the hardness of the wall 7 of the floor processing element 2, so that when the floor processing element 2 rotates, the fragrance element 10 does not audibly strike the wall 7 of the hollow space 3. The specific weight of the fragrance element 10 is also lower than that of the wall 7. The fragrance molecules accommodated in the fragrance element 10 can escape into the environment through the hollow space opening 4 along with an air flow generated during the rotation of the floor processing element 2. The generated air flow entrains the fragrance molecules, and distributes them in the air. The fragrance outside of the floor processing element 2 is more perceivable during the rotation of the floor processing element 2 than when the floor processing element 2 stands idle. As a consequence, the perception of the fragrance is linked to the operation of the floor processing device 1. Based on the fragrance perceivable within the environment, a user can thus discern that the floor processing device 1 has recently performed a floor processing operation, or is currently still performing a floor processing operation. As a result, the user can discern the cleaning efficiency of the floor processing device 1. When a fragrance can be perceived in the environment of the floor processing device 1, it denotes that the floor processing device 1 is in operation. If no fragrance can be perceived despite a planned use of the floor processing device 1, the absence of a fragrance informs the user either that an operation error of the floor processing device 1 is present, or that the service life of the fragrance element 10 has ended. The exterior of the wall 7 of the floor processing element 2 has a plurality of bristle elements 12, which here are configured to resemble bristle tufts, each having a plurality of bristles. During operation of the floor processing device 1, the bristle elements 12 serve to mechanically act on the surface to be cleaned. The service life of the bristle elements 12 as wear parts of the floor processing device 1 can preferably be linked with the service life of the fragrance element 10. The floor processing element 2, in particular its bristle elements 12, wears out as the operating time of the floor processing device 1 increases. The fragrance of the fragrance element 10 is here used as an indicator that the floor processing element 2 or bristle elements 12 have to be replaced. As soon as the user exchanges the floor processing element 2 along with the bristle elements 12 and fragrance element 10 for a new floor processing element 2, fragrance is once again released into the environment during operation of the floor processing device 1, so that the operation of the floor processing device 1 can once again be perceived by way of the fragrance.

Figure 3:
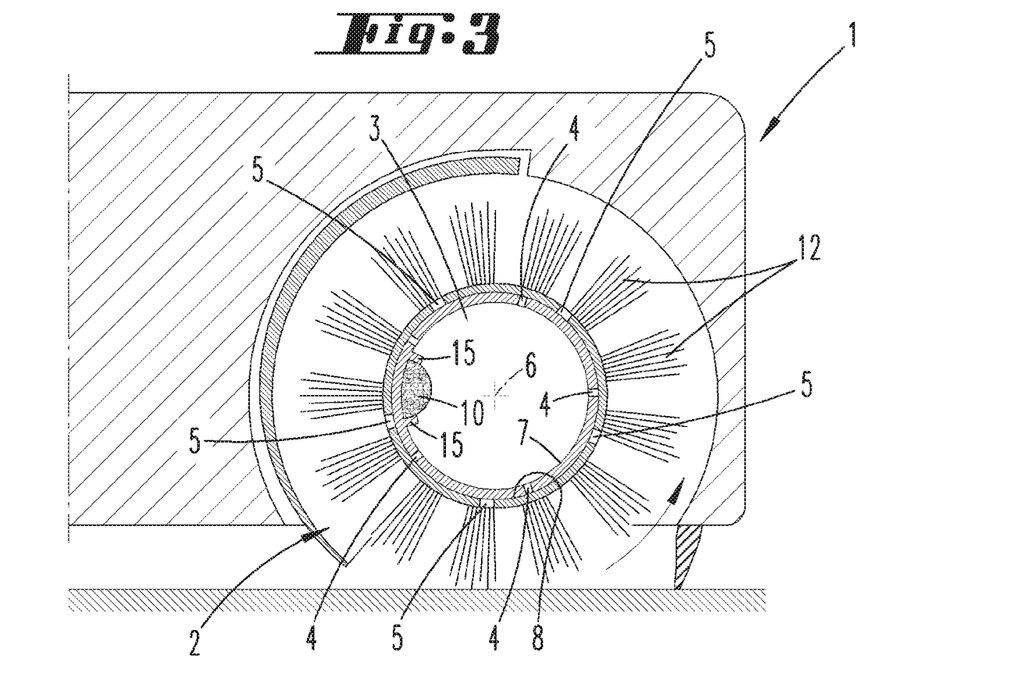
FIG. 3 is a cross section through a floor processing element according to a second embodiment.

FIG. 3 shows another embodiment of a floor processing element 2. A fragrance element 10 is non-rotatably arranged inside of the hollow space of this floor processing element 2 on the wall 7 bordering he hollow space. The fragrance element 10 is here fastened by way of fastening means 15, which hold the fragrance element 10 on the wall 7. As the floor processing element 2 rotates, the fragrance element 10 thus rotates along with the wall 7. Accordingly, the fragrance element 10 does not undergo a relative displacement within the hollow space 3. The fastening means 15 can provide a clamped connection or latched connection. However, it is also possible for the fragrance element 10 to be permanently fastened to the wall 7 of the floor processing element 2, for example adhesively bonded. If the floor processing element 2 is configured in such a way that the fragrance element 10 can be changed out, for example via an end face of the cylindrically designed floor processing element 2, it is recommended that the fastening means 15 reversibly fasten the fragrance element 10.

Figure 4:
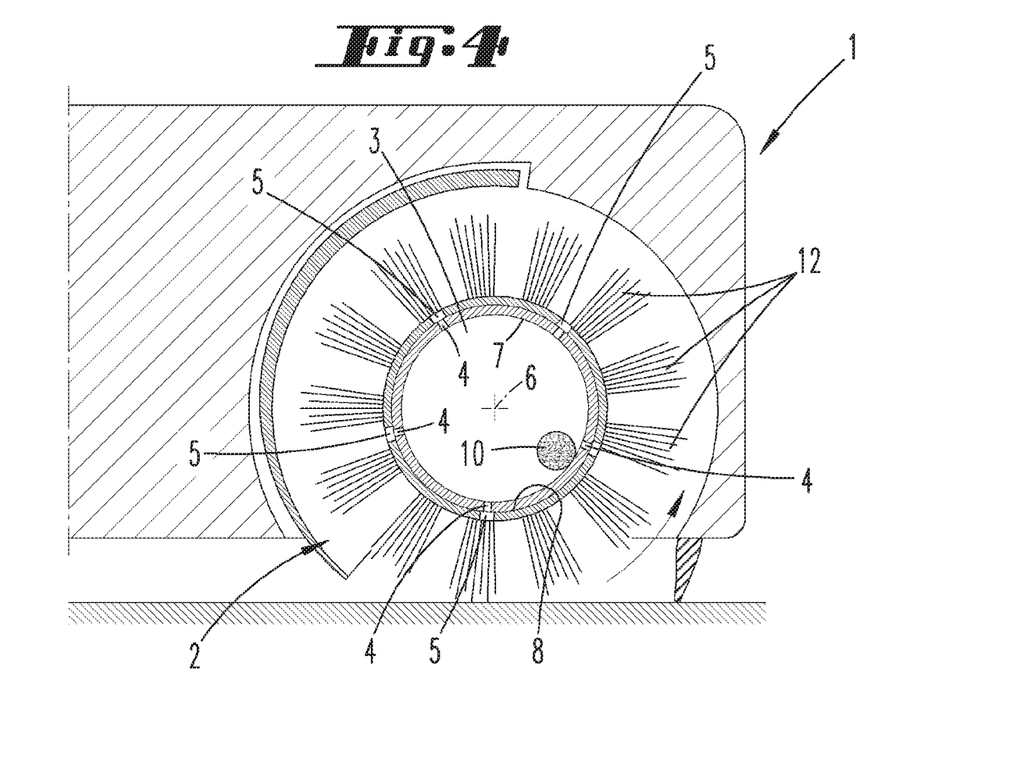
FIG. 4 is a cross section through a floor processing element according to a third embodiment at a first point in time during the rotation of the floor processing element.
Figure 5:
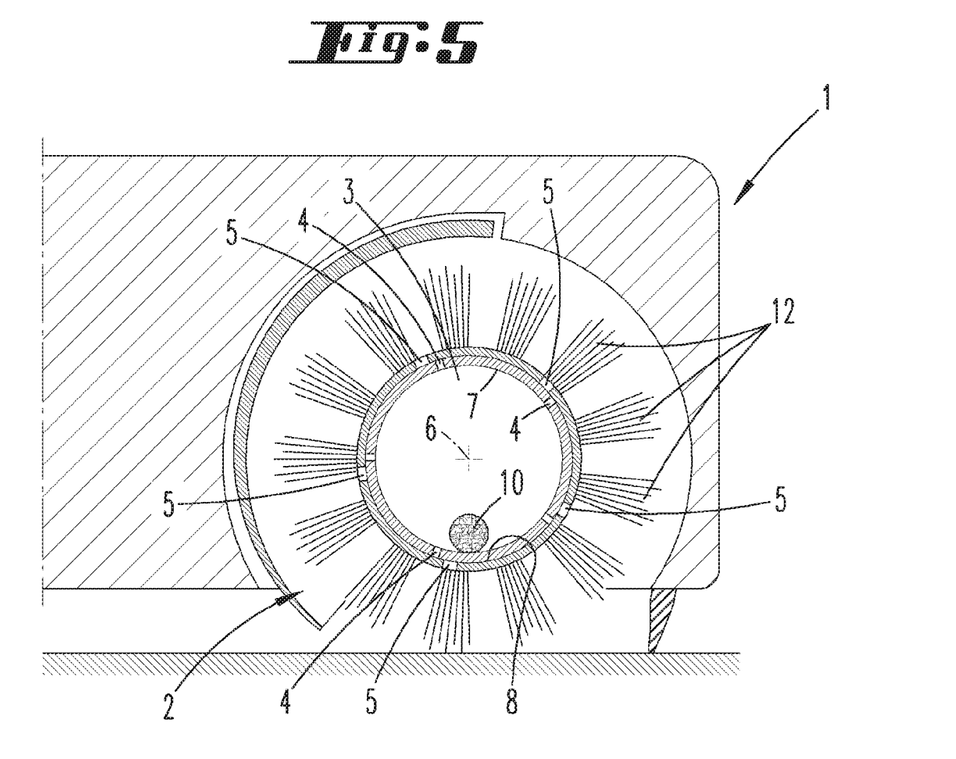
FIG. 5 is the floor processing element according to FIG. 4 at a second point in time during the rotation.
Figure 6:
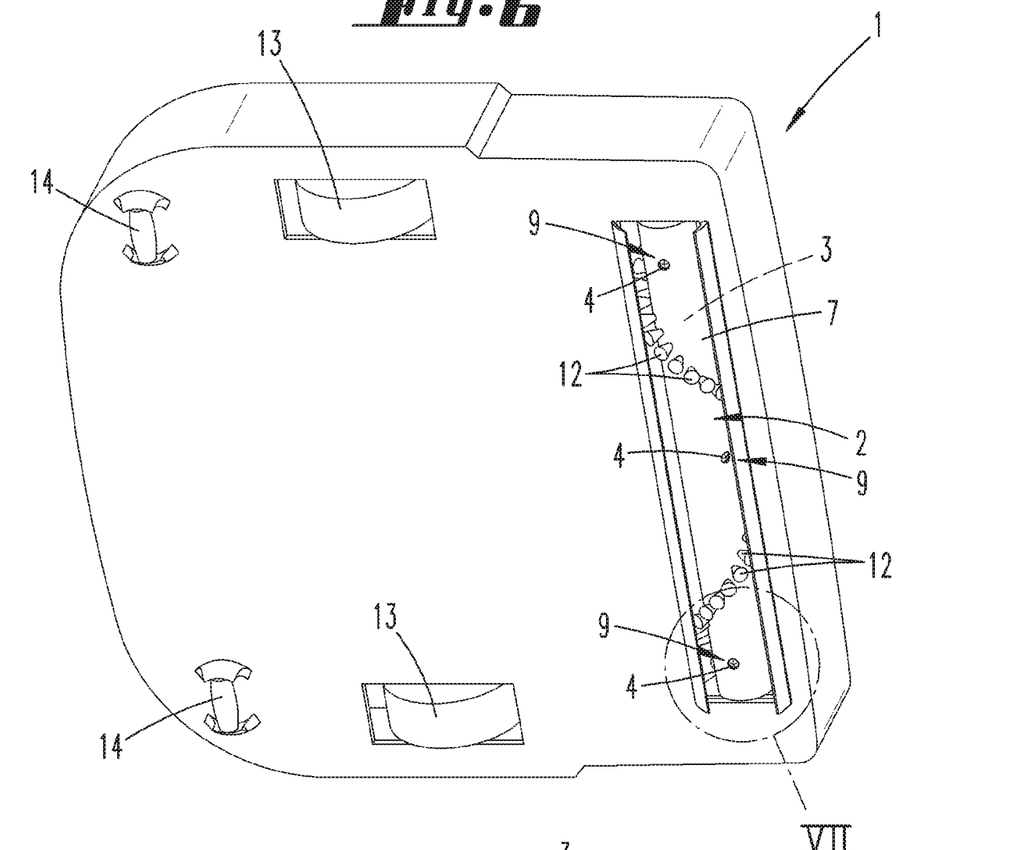
FIG. 6 is a bottom view of a floor processing device with a floor processing element according to a fourth embodiment.

FIGS. 4 and 5 show another embodiment of a floor processing element 2, which has two walls 7, 8 that can rotate relative to each other. A first wall 7 bordering the hollow space can here rotate relative to an outer second wall 8, the exterior of which has bristle elements 12. The first wall 7 and second wall 8 each have a plurality of hollow space openings 4 or 5. The walls 7, 8 are each shaped like a hollow cylinder, wherein the first wall 7 is arranged concentrically inside of the second wall 8. During operation of the floor processing device 1, the first, inner wall rotates relative to the outer, second wall 8 around the rotational axis 6, during which the position of the hollow space openings 4, 5 formed on the walls 7, 8 changes relative to each other. Rotational positions come about in which the hollow space openings 4, 5 are covered by partial areas of the respective other wall 7, 8, as do rotational positions in which corresponding hollow space openings 4, 5 of the walls 7, 8 lie one above the other, and thereby release a flow path between the hollow space 3 of the floor processing element 2 and the environment. During rotation of the floor processing element 2, the hollow space openings 4, 5 thus overlap regularly or irregularly, and let the fragrance molecules pass. With the floor processing element 2 standing idle, the probability that the hollow space openings 4, 5 will overlap must be kept low, for example via a defined rest position of the floor processing element 2, thereby preventing fragrance molecules from exiting the hollow space 3 of the floor processing element 2. The floor processing device 1 thus only releases the fragrance with the floor operating device 1 in operation, with it otherwise not being perceivable. As a consequence, the user is provided with clear information as to whether the floor processing device 1 is or was operating or not. FIGS. 4 and 5 show various rotational positions of the walls 7, 8 of the floor processing element 2. FIG. 4 here depicts a rotational position in which the corresponding hollow space openings 4, 5 of the first wall 7 and second wall 8 overlap, and thereby release a flow path from the hollow space 3 into the environment. By contrast, FIG. 5 presents a rotational position of the floor processing element 2 in which the hollow space openings 4 of the first wall 7 are covered by the second wall 8, or the hollow space openings 5 of the second wall 8 are covered by the first wall 7. The flow path from the hollow space 3 to the environment is thus closed off.

FIGS. 6 to 9 show another embodiment of a floor processing device 1 according to the invention. The floor processing device 1 has the usual two electric motor-driven wheels 13, with which the floor processing device 1 moves on the surface to be cleaned. The bottom of the depicted floor processing device 1 further has two support rollers 14. The floor processing element 2 is here also designed as a cleaning roller provided with bristle elements 12. A wall 7 of the floor processing element 2 once again borders an inner, cylindrical hollow space 3 of the floor processing element 2. The wall 7 has several hollow space openings 4, which each have a valve element 9. The valve element 9 is mechanically activatable, and can either block or release the hollow space opening 4 as a function of an acting centrifugal force during rotation of the floor processing element 2. The valve element 9 is comprised of an elastically configured edge area of the wall 7. For example, the valve element 9 here consists of a rubber material, which can be displaced toward a closed position or open position, depending on the restoring force intrinsic to the material and the level of centrifugal force. The centrifugal force acting radially inwardly on the valve element 9 causes the edge areas of the hollow space opening 4 to elastically deform radially outward (relative to the rotational axis 6), thereby releasing the hollow space opening 4 for an air flow to exit the hollow space 3. As soon as the centrifugal force drops below a defined minimum speed owing to a reduction in the speed of the floor processing element, the restoring force of the valve element 9 predominates, so that the valve element 9 is displaced back into the closed position. The valve element 9 is here designed as a single part with the remaining partial areas of the wall 7. For example, the valve element 9 is injection molded onto the wall 7.

Figure 7:
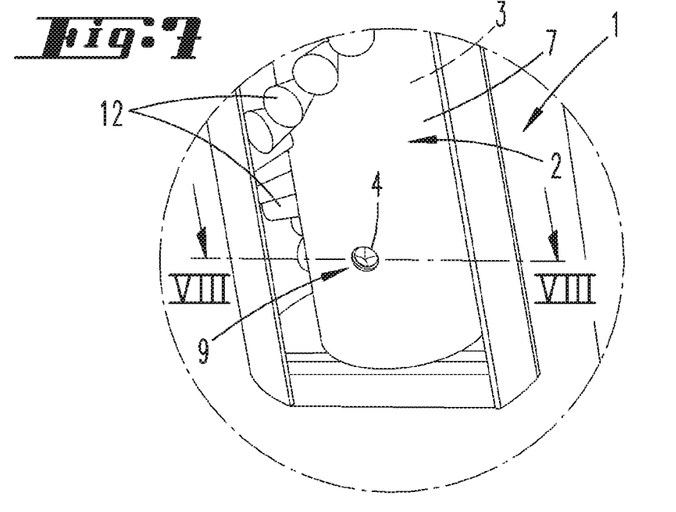
FIG. 7 is an enlarged partial area of the floor processing element according to FIG. 6.
Figure 8:
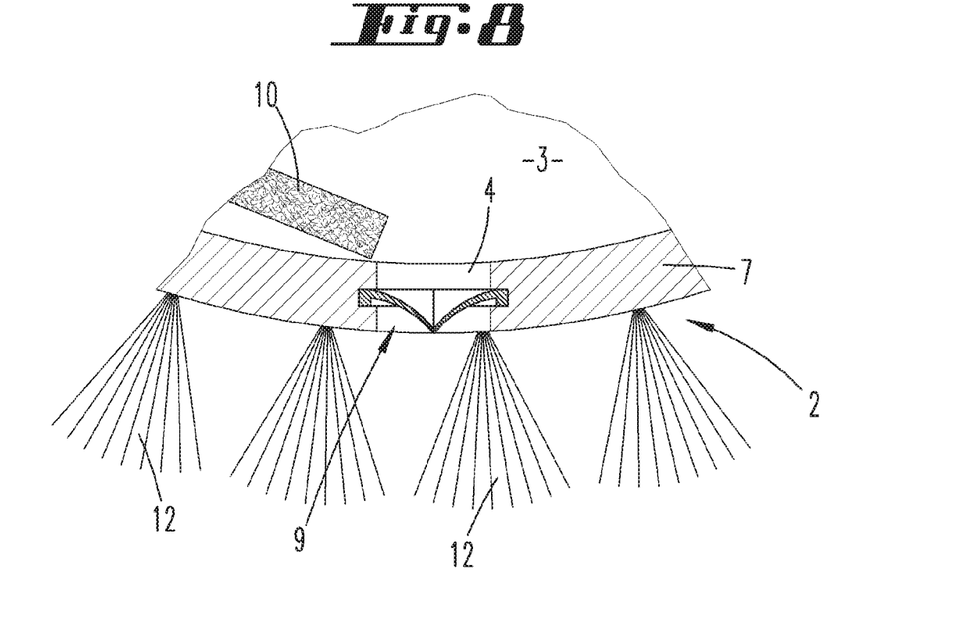
FIG. 8 is a cross section through the enlarged partial area of the floor processing element according to FIG. 7, with a closed valve element.

FIG. 7 shows a magnified partial area of the floor processing element 2 with closed valve element 9. FIG. 8 shows a cross section of the valve element 9 perpendicular to the longitudinal extension of the rotational axis 6.

Figure 9:
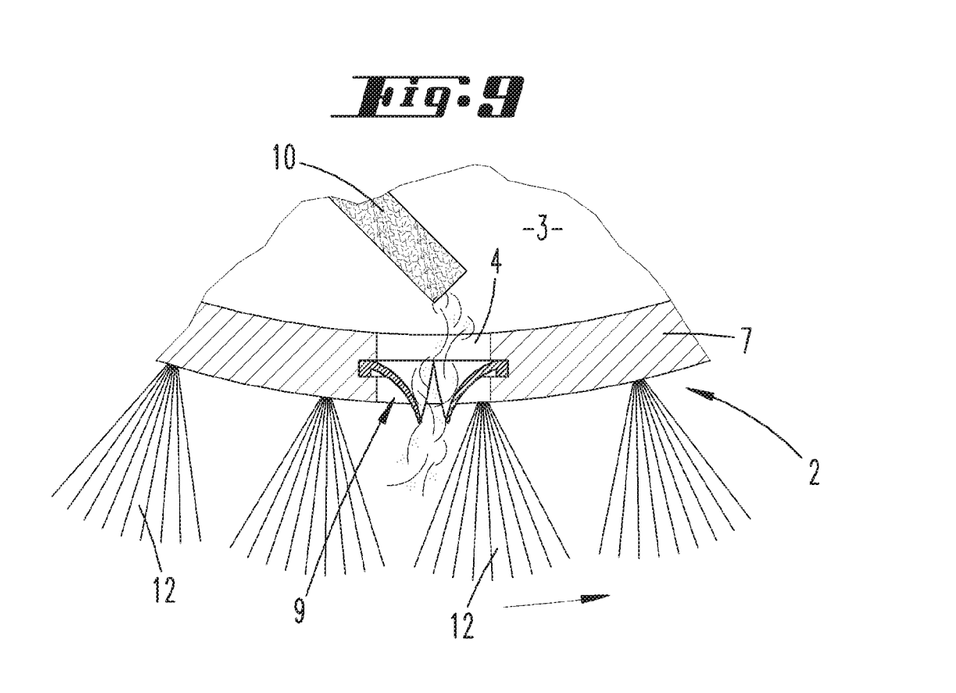
FIG. 9 is the partial area of the floor processing element according to FIG. 8 with an open valve element.

Finally, FIG. 9 shows a cross section of the open valve element 9, which is opened radially outward due to the centrifugal force acting on the valve element 9 during the rotation of the floor processing element 2, so that the fragrance molecules released by the fragrance element 10 can get through the hollow space opening 4 and into the environment of the floor processing device 1.

REFERENCE LIST

1 Floor processing device
2 Floor processing element
3 Hollow space
4 Hollow space opening
5 Hollow space opening
6 Rotational axis
7 Wall
8 Wall
9 Valve element
10 Fragrance element
11 Distance measuring device
12 Bristle element
13 Wheel
14 Support roller
15 Fastening means

What is claimed is:

1. A floor processing device comprising:
a device housing,
a motor-driven floor processing element for processing a floor to be processed, wherein the floor processing element is movable relative to the housing and has a hollow space with a hollow space opening that joins the hollow space with the ambient air, and
a fragrance element that is designed as a solid body and arranged in the hollow space, wherein the hollow space of the floor processing element has a volume that corresponds to a multiple of a volume of the fragrance element.

2. The floor processing device according to claim 1, wherein the floor processing device is a cleaning roller that is configured to rotate around a rotational axis.

3. The floor processing device according to claim 1, wherein a service life of the fragrance element essentially corresponds to a service life of a wear part of the floor processing device.

4. The floor processing device according to claim 3, wherein the wear part is comprised of bristle elements arranged on the floor processing element.

5. The floor processing device according to claim 1, wherein a material of the fragrance element has a lower hardness than a material of a wall bordering the hollow space.

6. The floor processing device according to claim 5, wherein the fragrance element is made out of a foam.

7. The floor processing device according to claim 1, wherein the fragrance element is configured to move freely inside of the hollow space.

8. The floor processing device according to claim 1, wherein the fragrance element is non-rotatably arranged on a wall bordering the hollow space.

9. The floor processing device according to claim 1, wherein the hollow space is bordered by two walls that lie one inside the other and are displaceable relative to each other, wherein a first one of said walls has a first hollow space opening, and a second one of said walls has a second hollow space opening, and wherein the walls are configured such that a displacement of the walls relative to each other enables the first hollow space opening to be closed or opened by the second wall and the second hollow space opening to be closed or opened by the first wall.

10. The floor processing device according claim 1, further comprising a mechanically activatable valve element allocated to the hollow space opening, wherein the valve element is configured such that depending on a level of centrifugal force acting on the valve element due to a rotation of the floor processing element, the valve element can be displaced into a closing position that closes the hollow space opening and/or into an opening position that releases the hollow space opening.

11. The floor processing device according to claim 10, wherein the valve element is designed to release the hollow space opening once a minimum speed of the floor processing element has been reached.

12. The floor processing device according to claim 10, wherein the valve element has a restoring element, and/or wherein the valve element is designed as a restoring element, and wherein a restoring force of the restoring element acts opposite a centrifugal force of the floor processing element in the direction of the closed position.

* * * * *